US00RE48536E

(19) United States
(12) Reissued Patent
Imhof et al.

(10) Patent Number: US RE48,536 E
(45) Date of Reissued Patent: Apr. 27, 2021

(54) COLLAGEN SPONGE

(71) Applicant: Geistlich Pharma AG, Wolhusen (CH)

(72) Inventors: Cornel Imhof, Lucerne (CH); Lothar Schloesser, Lucerne (CH); Niklaus Stiefel, Lucerne (CH); Martin Wuest, Emmenbrücke (CH)

(73) Assignee: Geistlich Pharma, Wolhusen (CH)

(21) Appl. No.: 16/364,805

(22) Filed: Mar. 26, 2019

Related U.S. Patent Documents

Reissue of:
(64) Patent No.: 9,655,997
Issued: May 23, 2017
Appl. No.: 14/969,158
Filed: Dec. 15, 2015

(30) Foreign Application Priority Data

Dec. 15, 2014 (EP) ..... 14197987

(51) Int. Cl.
*A61L 27/56* (2006.01)
*A61L 27/26* (2006.01)
*A61L 27/36* (2006.01)

(52) U.S. Cl.
CPC ..... *A61L 27/56* (2013.01); *A61L 27/26* (2013.01); *A61L 27/362* (2013.01); *A61L 27/3604* (2013.01); *A61L 27/3625* (2013.01); *A61L 27/3629* (2013.01); *A61L 27/3683* (2013.01); *A61L 27/3687* (2013.01); *A61L 27/3691* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 2004/0265785 | A1 | 12/2004 | Damink | |
| 2008/0057126 | A1* | 3/2008 | Fischer | A61L 27/48 424/484 |
| 2012/0010146 | A1* | 1/2012 | Han | A61K 8/64 514/17.2 |

FOREIGN PATENT DOCUMENTS

| | | | |
|---|---|---|---|
| EP | 1561480 | A2 | 8/2005 |
| EP | 1676592 | A1 | 7/2006 |
| EP | 1676592 | B1 | 1/2013 |
| EP | 3055000 | B1 | 12/2016 |
| WO | 2012084214 | A1 | 6/2012 |

OTHER PUBLICATIONS

Boekema et al., "Effect of pore size and cross-linking of a novel collagen-elastin dermal substitute on wound healing" Journal of Material Sciences: Materials in Medicine, vol. 25, (2014), pp. 423-433, XP002740386.

Cairo et al. "Treatment of gingival recession with coronally advanced flap procedures: a systematic review" J. Clin. Periodontal. 35 (Suppl. 8) (2008), pp. 136-162 (abstract).

Jung et al. "Postextraction tissue management: a soft tissue punch technique" Int J Periodontics Restorative Dent 24(6) (2004) pp. 545-553. (Abstract).

International Search Report and Written Opinion of the International Searching Authority issued in International Application No. PCT/EP2015/079754, dated Jun. 20, 2017, 12 pages.

Intention to Grant Communication Under Rule 71(3) EPC issued in corresponding European Application No. 15808663.7, dated Sep. 28, 2016, 36 pages.

Notice of Allowance in corresponding Canadian Application CA2,970,849, dated Feb. 6, 2019, 1 page.

Notification of Grant in corresponding Singapore application No. 11201704864Y, dated Jul. 4, 2018, 2 pages.

Notice of Acceptance in corresponding Australian application No. 2015367710, Jul. 2, 2018, 3 pages.

Cairo et al. "Soft Tissue Management at implant sites" J. Clin. Periodontol. 35 (Suppl. 8) (2008), pp. 163-167 (abstract).

Extended European Search Report in application No. EP14197987.2 dated Jun. 26, 2015.

Hafemann et al. "Cross-linking by 1-ethyl-3 (3-dimethylaminopropyl)-carbodiimide (EDC) of a collagen/elastin membrane meant to be used as a dermal substitute: effects on physical, biochemical and biological features in vitro", Journal of Materials Science: Materials in Medicine, vol. 12, No. 5, 1 (2001), pp. 437-446, XP055193133.

Mathes et al. "A bioreactor test system to mimic the biological and mechanical environment of oral soft tissues and to evaluate substitutes for connective tissue grafts" Biotechnology and Bioengineering, vol. 107, No. 6, 15 (2010), pp. 1029-1039, XP055191964.

Thoma et al. "Soft tissue volume augmentation by the use of collagen-based matrices in the dog mandible: a histological analysis." J. Clin. Periodontol.: 38: (2011), pp. 1063-1070 (Abstract).

Thoma et al. "A systematic review assessing soft tissue augmentation techniques" Clin. Oral Impl. Res. 20 (Supp. 4) 2009, pp. 146-165.

(Continued)

*Primary Examiner* — Kevin S Orwig

(74) *Attorney, Agent, or Firm* — Rothwell, Figg, Ernst & Manbeck, P.C.

(57) ABSTRACT

A resilient resorbable chemically crosslinked collagen sponge for promoting soft tissue volume augmentation in the oral region, comprising 60-96% (w/w) collagen and 4-40% (w/w) elastin, which shows by mercury intrusion porosimetry interconnected pores with a median pore diameter between 50 and 90 μm and at least 80% porosity with a pore diameter more than 10 μm, an onset temperature of 45 to 57° C. and a density in dry state from 50 to 65 mg/cm$^3$. A process for preparing a resilient resorbable chemically crosslinked collagen sponge. A method of using a resilient resorbable chemically crosslinked collagen sponge as an implant in the oral cavity for soft tissue volume augmentation.

27 Claims, 1 Drawing Sheet

(56) References Cited

OTHER PUBLICATIONS

International Search Report and Written Opinion of the International Searching Authority issued in International Application No. PCT/EP2015/079754, dated Feb. 12, 2016, 14 pages.
Intention to Grant Communication Under Rule 71(3) EPC issued in corresponding European Application No. 15808663.7, dated Sep. 28, 2016, 37 pages.

* cited by examiner

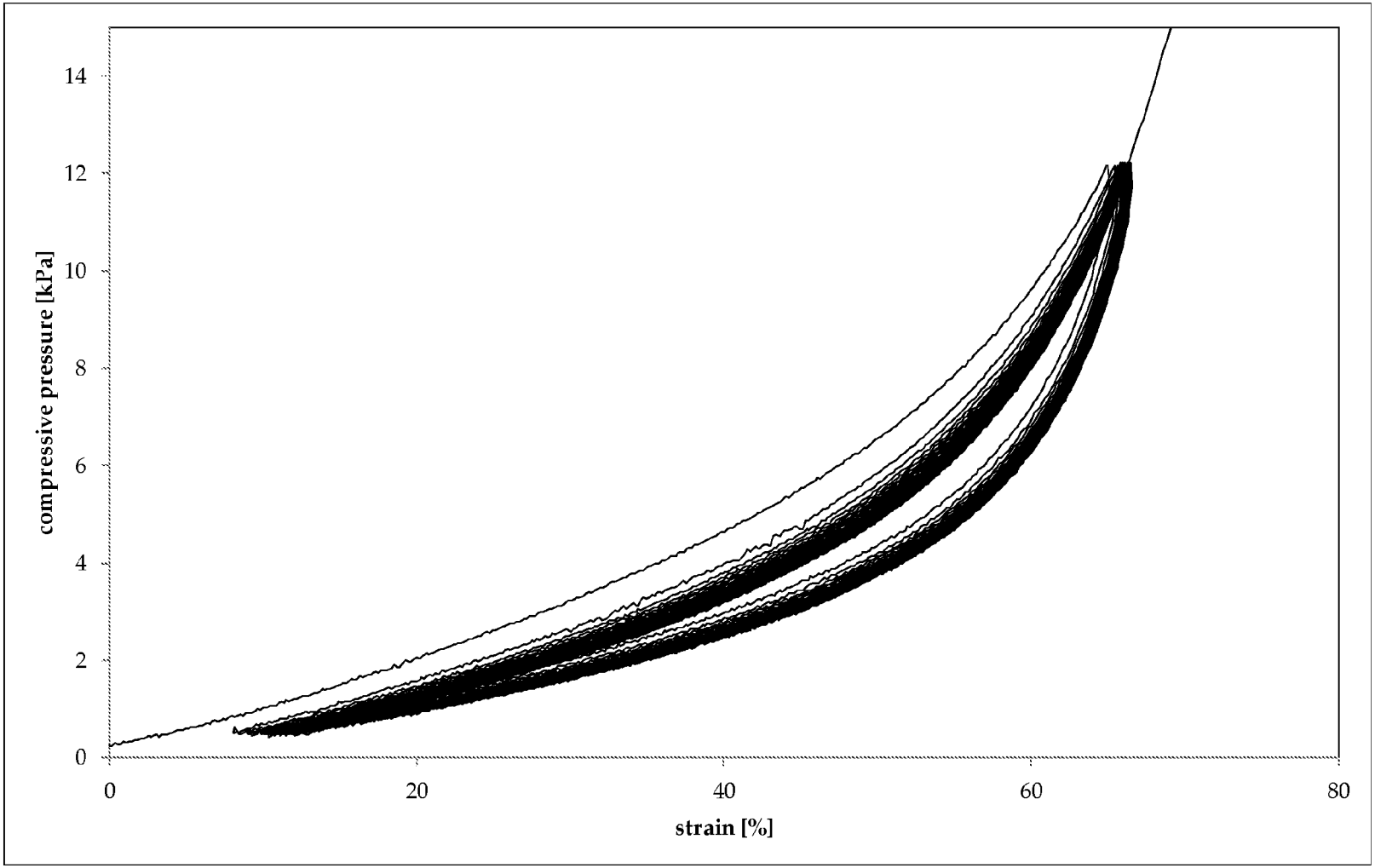
compressive pressure [kPa]
0
2
4
6
8
10
12
14
0
20
40
60
80
strain [%]

COLLAGEN SPONGE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the benefit of European Patent Application No. 14197987.2 filed on Dec. 15, 2014, the disclosure of which is incorporated by reference in its entirety.

FIELD OF THE INVENTION

The invention relates to a new resilient resorbable chemically crosslinked collagen sponge for promoting soft tissue volume augmentation in the oral region, a process for preparing that resilient resorbable chemically crosslinked collagen sponge and the use thereof as an implant in the oral cavity for soft tissue volume augmentation.

BACKGROUND OF THE INVENTION

Soft tissue volume augmentation has become one of the major challenges in dental and cranio-maxillofacial surgery. In order to improve both functional and esthetic outcomes by soft tissue volume augmentation, autogenous tissue grafts such as the free gingival graft (FGG) or the subepithelial connective tissue graft (SCTG), despite their drawbacks are still broadly used for various indications and considered to be the gold standard (F. Cairo et al., 2008, J. Clin. Periodontol. 35 (Suppl. 8), 314-319; R. Jung et al., 2004, Int. J. Periodontics Restorative Dent. 24(6), 545-553 and D. Thoma, 2009, Clin. Oral Implants Res. 20 (suppl. 4), 146-165). However, the harvesting procedure for autogenous tissue at a second surgical site usually in the palate has drawbacks for the patient and limitations as to the quality and quantity of tissue that can be retrieved.

A regenerative device for promoting soft tissue volume augmentation in the oral region is thus desirable.

Gingival cells of the oral connective tissue are exposed to complex mechanical forces during mastication, swallowing, tongue movement, speech, tooth movement and orthodontic treatment. Especially during wound healing following surgical procedures, internal and external forces may occur, creating pressure upon the regenerative device and newly formed tissue.

A regenerative device has to meet certain criteria before being used in the oral cavity for soft tissue volume augmentation: It must be biocompatible, resorbable in vivo, allow gingival ingrowth, show a good level of tissue integration such as to allow uneventful healing (without excessive inflammation or dehiscence) and be able to withstand mechanical forces by acting as a scaffold that maintains tissue volume during a sufficient time during the wound healing process after implantation, generally at least about 3 months.

No such regenerative device has so far been disclosed in the prior art.

H. Mathes et al. in "A Bioreactor Test System to mimic the Biological and Mechanical Environment of Oral Soft Tissues and to Evaluate Substitutes for Connective Tissue Gaffs", 2010, Biotechnology and Bioengineering, Vol. 9999, No. 9999, disclose that such properties of a regenerative device consisting of a collagen sponge might be achieved by stiffening the matrix body by crosslinking of the collagen fibers to a degree allowing the right balance between mechanical stability (high degree of crosslinking) and uneventful soft tissue healing (low degree of crosslinking), but are totally silent on how to prepare such a collagen sponge. They disclose that three different collagen sponge prototypes consisting of porcine collagen type I and Ill with an average pore diameter of 92 μm and 93% porosity and differing in their degree of crosslinking (prototypes provided by Geistlich Pharma, Wolhusen, Switzerland) showed after culture under mechanical stimulation for 14 days a satisfying volume retention with a good fibroblast cell vitality.

DS Thoma et al. in "Soft tissue volume augmentation by the use of collagen-based matrixes: a volumetric analysis", 2010, J. of Clin. Periodontology 37, 659-666, and "Soft tissue volume augmentation by the use of collagen-based matrixes in a dog mandible—a histological analysis", 2011, J. Clin. Periodontol.: 38:1063-1070, disclose that one of the collagen sponge prototypes referred to in the above publication of H. Mathes et al. showed after a period of 28 or 84 days of implementation into a chronic ridge defect of a dog mandible the same volume retention as the gold standard, SCTG (subendopithelial connective tissue graft).

The prior art does not disclose or suggest what are the features of such a chemically crosslinked collagen sponge prototype, or of any other regenerative collagen device fulfilling the criteria set forth above for a use in the oral cavity for soft tissue volume augmentation, or how such a device can be prepared.

EP-1561480 discloses a resorbable collagen device for use as a dural substitute for growing meningeal tissue, comprising a chemically crosslinked collagen sheet which has a majority of pores below 10 μm and a method for preparing that collagen device comprising the steps of mixing collagen with water under such conditions that the mixture contains substantially solubilized collagen, lyophilizing the mixture into a collagen device and chemically crosslinking the collagen device, using as crosslinking agent formaldehyde or gluteraldehyde. A dural substitute is not, like a regenerative device for promoting soft tissue volume augmentation in the oral region, exposed during wound healing to pressure created by the above mentioned complex mechanical forces.

US-2004-0265785 describes a process for producing a collagen-elastin membrane containing at least 20% (w/w) elastin, comprising the steps of first chemically removing hydrophobic accompanying substances from an elastin containing collagen material of natural origin, then chemically removing non-hydrophobic substances. The collagen-elastin product is not chemically crosslinked.

Boekema B. K. L. H. et al., 2014, Journal of Material Sciences: Materials in Medicine, Feb. 2014 25: 423-433, describe the effect on wound healing of pore size and crosslinking on collagen-elastin scaffolds used as dermal substitutes. The disclosed EDC-NHS chemically crosslinked scaffolds contain 10-15% elastin, have a pore size of 80 to 120 μm and a denaturation temperature of 64 to 69° C. (see Table 1, page 425). They are sterilized by ethylene oxide gas treatment. The authors conclude that crosslinking negatively affects wound healing on several important parameters, notably by reducing the ability of fibroblasts to proliferate and replace the dermal substitute by new tissue. A dermal substitute is not, like a regenerative device for promoting soft tissue volume augmentation in the oral region, exposed during wound healing to pressure created by the above mentioned complex mechanical forces.

The problem or objective of the invention is to find a regenerative collagen device for promoting soft tissue volume augmentation in the oral region that is biocompatible, resorbable in vivo, allows gingival ingrowth, shows a good level of tissue integration such as to allow uneventful healing (without excessive inflammation or dehiscence) and be able to withstand mechanical forces by acting as a scaffold that maintains tissue volume during a sufficient time during the wound healing process after implantation, generally at least about 3 months.

The above problem is solved by the invention as defined in the appended claims.

BRIEF SUMMARY OF THE INVENTION

The invention relates to a resilient resorbable chemically crosslinked collagen sponge for promoting soft tissue volume augmentation in the oral region, comprising 60-96% (w/w) collagen and 4-40% (w/w) elastin, which shows by mercury intrusion porosimetry interconnected pores with a median pore diameter between 50 and 90 μm and at least 80% porosity with a pore diameter more than 10 μm, an onset temperature of 45 to 57° C. and a density in dry state from 50 to 65 mg/cm$^3$.

The chemically crosslinked collagen sponge comprises 60-96% (w/w) collagen and 4-40% (w/w) elastin. The elastin content is here measured by desmosine/iodesmosine determination according to a modification of a known method involving hydrolysis and RP-HPLC (see e.g. Guida E. et al. 1990 Development and validation of a high performance chromatography method for the determination of desmosines in tissues in Journal of Chromatography or Rodriguqe P 2008 Quantification of Mouse Lung Elastin During Prenatal Development in The Open Respiratory Medicine Journal). To determine the desmosine/isodesmosine content of dry elastin, the elastin of the sponge is subjected to elastin isolation procedures as described by Starcher and Galione 1976 Purification and Comparison of Elastin from Different Animal Species in Analytical Biochemistry.

That sponge is suitably derived from tissues of natural origin which contain such proportions of collagen and elastin. Examples of such tissues include mammalian (e.g. porcine or bovine) peritoneum or pericardium membrane, placenta membrane, small intestine submucosa (SIS) and dermis. Usually the collagen is predominantly collagen type I, collagen type III or a mixture thereof. The collagen may also include a proportion of notably collagen type II, type IV, type VI or type VIII or any combination of those or any collagen types.

BRIEF DESCRIPTION OF THE SEVERAL VIEWS OF THE DRAWING

The FIGURE shows the typical result of a cyclic compression test.

DETAILED DESCRIPTION OF THE INVENTION

The term "collagen" used in this application usually refers to that combination of 60-96% (w/w) collagen and 4-40% (w/w) elastin.

Preferably the chemically crosslinked collagen sponge comprises 70-90% (w/w) collagen and 10-30% (w/w) elastin.

An example of a suitable starting material for preparing such a chemically crosslinked collagen sponge is a slurry of collagen fibres from the membrane prepared from porcine or bovine peritoneum by a process similar to that described in "Example" of EP-B1-1676592 or from the membrane Geistlich Bio-Gide® (obtainable from Geistlich Pharma A.G., Switzerland) prepared from porcine peritoneum by a very similar process and/or a slurry of collagen fibres prepared from porcine dermis by a process similar to that described in Example 7 of WO 2012/084214.

The above resilient resorbable chemically crosslinked collagen sponge promotes soft tissue augmentation in the oral region by fostering ingrowth of gingival cells while keeping volume after loading and unloading of mechanical stresses.

For fostering ingrowth of gingival cells the chemically crosslinked collagen sponge must have a high porosity (pore volume fraction) in an appropriate diameter range for gingival fibroblasts to grow. It has been found that this ingrowth is suitably fostered when the sponge shows by mercury intrusion porosimetry interconnected pores with a median pore diameter between 50 and 90 μm and at least 80%, preferably at least 90%, porosity with a pore diameter more than 10 μm. The chemically crosslinked sponge with such a distribution of pores is suitably prepared by a process comprising mixing before crosslinking in appropriate proportions a slurry of collagen fibres from the membrane prepared from porcine or bovine peritoneum as disclosed in the previous paragraph and a slurry of collagen fibres prepared from porcine dermis as disclosed in the previous paragraph.

The term "resilient" here means that the chemically crosslinked collagen sponge is resistant to pressure, i.e. capable of regaining a large part of its original volume after being submitted to pressure in vitro or in vivo.

For keeping volume in the oral region the resilient resorbable chemically crosslinked sponge must be able to withstand the complex mechanical forces induced by mastication, tongue movement, speech and tooth movement by acting as a scaffold that maintains tissue volume during a sufficient time during the healing process after implantation, generally about 3 months. It has been found that this in vivo resilient behaviour of the implant is attained when, in an in vitro mechanical test of cyclic compression at a temperature of 37° C. of the collagen sponge wetted by a phosphate buffer saline (PBS) solution designed to mimic the body fluids, the thickness retention in respect to the initial thickness is at least 70%, preferably at least 80%, more preferably at least 85%, or the hysteresis retention in respect of the first loading is less than 55%, preferably less than 45%, after 49 cycles of compression to a pressure of 12.1 kPa.

It has been found that the above in vitro thickness retention of at least 70% and hysteresis retention of less than 55% combined with in vivo healing without excessive inflammation or dehiscence is attained when the sponge shows an onset temperature from 45 to 57° C. and a density in dry state from 50 to 65 mg/cm$^3$.

The onset temperature is measured by DSC on the collagen sponge wetted with a buffer solution according to US Pharmacopia standard: Ph. Eur. 2.2.34, USP <891> (buffer composition for 1 litre of water: 8 g sodium chloride, 0.2 g potassium phosphate, 1.15 g sodium phosphate and 0.2 g potassium chloride; start temperature 15° C., end temperature 90° C., heating rate 5° C./min). This parameter reflects the crosslinking degree of the sponge. The onset temperature is closely linked to the sponge in vitro resistance to cyclic compression (thickness retention or hysteresis retention in the mechanical test of cyclic compression), in vivo resilience (keeping of tissue volume during a sufficient time during the healing process after implantation) and good integration into the surrounding tissues (no excessive inflammation or dehiscence).

The required in vitro resistance to cyclic compression and the in vivo resilience combined with in vivo healing without without excessive inflammation or dehiscence can be attained when the onset temperature is from 45 to 57° C., preferably from 46 to 53° C. When the onset temperature is below 46° C., the in vitro resistance to cyclic compression and the in vivo resilience may not be sufficient. When the onset temperature is above 57° C., there is a substantial risk of adverse events such as excessive inflammation and/or dehiscence appearing after implantation.

The density in dry state, measured by weighing and measuring the volume of the collagen sponge after extensive lyophilisation (as described in detail below), is another essential or critical parameter for reaching the required in vitro resistance to cyclic compression and the in vivo resilience combined with in vivo healing without without excessive inflammation or dehiscence. Those features can be attained when the density in dry state is from 50 to 65, preferably from 50 to 60 mg/cm$^3$. When the density in dry state is below 50 mg/cm$^3$, the in vitro resistance to cyclic compression and the in vivo resilience may not be sufficient. When the density in dry state is above 65 mg/cm$^3$, there is a risk of adverse events such as excessive inflammation and/or dehiscence appearing after implantation.

The term "resorbable" here means that the chemically crosslinked collagen sponge is capable of being resorbed in vivo notably through the action of collagenases and elastases. A controlled in vivo resorbability of the chemically crosslinked collagen sponge is essential to healing without excessive inflammation or dehiscence. The enzymatic degradation test using collagenase from Clostridium histolicum described in detail below gives an excellent prediction of the in vivo resorbability.

In that test, for all samples of the sterile resilient resorbable chemically crosslinked collagen sponge according to the invention that in vivo showed interesting volume retention and healing without adverse advents such as excessive inflammation or dehiscence, the collagen was completely degraded in 3 to 5 hours. The above resilient resorbable chemically crosslinked collagen sponge is suitably prepared from tissues of natural origin by a process comprising freeze drying and chemical crosslinking. Appropriate tissues of natural origin include porcine or bovine peritoneum or pericardium membranes, porcine or bovine placenta membrane and porcine or bovine SIS or dermis. Preferably the tissues of natural origin include porcine or bovine peritoneum membrane and porcine dermis. The above process comprising freeze drying and chemical crosslinking is generally followed by a sterilization step, which is suitably γ irradiation or X-ray sterilization.

The chemical crosslinking may be performed using any pharmaceutically acceptable crosslinking agent capable of giving to the resilient resorbable chemically crosslinked collagen sponge the required thickness retention in respect to the initial thickness or hysteresis retention in respect to the first loading in the cyclic compression test. Suitable such crosslinking agents include gluteraldehyde, formaldehyde, acetaldehyde, 1,4-butane diglycidyl ether (BDDGE), N-sulfosuccinimidyl-6-(4'-azido-2'-nitrophenylamino) hexanoate, hexamethylene diisocyanate (HMDC), cynamide, diphenylphosphorylazide, genipin, EDC (1-ethyl-3-(3-dimethylaminopropyl)-carbodiimide) and a mixture of EDC and NHS (N-hydoxysuccinimide). Small amounts or traces of the unreacted crosslinking agent or typical direct reaction products thereof can usually be detected in the resilient resorbable chemically crosslinked collagen sponge.

Preferably the chemical crosslinking is performed using a crosslinking agent selected from gluteraldehyde, EDC (1-ethyl-3-(3-dimethylaminopropyl)-carbodiimide) and a mixture of EDC and NHS (N-hydoxysuccinimide). Interesting prototypes of resilient resorbable chemically crosslinked collagen sponges according to the invention have indeed been prepared using each of those crosslinking agents.

More than 1000 different prototypes of collagen sponges have been prepared using as a crosslinking agent EDC or a mixture of EDC and NHS and tested in various in vitro tests and/or in vivo animal tests notably in mice, rats, rabbits and dogs. Preferably the chemical crosslinking is performed using one of those two crosslinking agents.

The resilient resorbable collagen sponge of the invention has been notably tested in:

an animal study involving measurement of mucosa volume gain by implantation into chronic defects of mandibles of dogs in comparison with the gold standard SCTG (Subepithelial Connective Tissue Graft), and a clinical study to investigate its performance and safety in tissue augmentation procedures to gain mucosal thickness around dental implants in the oral cavity in comparison with the gold standard for soft tissue volume augmentation SCTG (Subepithelial Connective Tissue Graft).

In both of those studies the resilient resorbable chemically crosslinked collagen sponge of the invention showed after 3-month-implantation an excellent integration into the surrounding tissues without excessive inflammation or dehiscence, the same safety and the same (i.e. not statistically different) soft tissue volume retention as SCTG.

The above resilient resorbable chemically crosslinked collagen sponge may be prepared by a process comprising the steps of:

(a) Submitting a porcine or bovine peritoneum or pericardium membrane to a basic treatment in a sodium hydroxide solution at a pH above 12, an acid treatment in a hydrochloric solution of pH of 1 to 3, a dehydrating treatment with a water soluble organic solvent and a degreasing treatment with an organic solvent, milling the dry membrane obtained with a cutting mill, sieving through a 0.5-2 mm sieve and suspending the powder obtained in an acidified water solution of pH from 2.5 to 3.5, such as to obtain a slurry of collagen fibres, (b) Submitting grinded bovine or porcine dermis to a dehydrating treatment with a water soluble organic solvent, a degreasing treatment with an organic solvent, a basic treatment in a strong inorganic base at a pH above 12, an acid treatment in a strong inorganic acid at a pH from 0 to 1, rinsing with water and suspending the collagen fibres, freeze-drying, cleaning the dried collagen fibres with an organic solvent and grinding the cleaned dried fibres in an acidified solution of pH from 3 to 4, such as to obtain a slurry of collagen fibres, (c) Mixing 3.5 to 4.5 parts of the slurry of collagen fibres obtained in (a) with 0.5 to 1.5 parts of the slurry of collagen fibres obtained in (b), such as to obtain a resulting slurry, (d) Freeze-drying the resulting slurry obtained in (c) and crosslinking the freeze-dried product in a solution containing a crosslinking agent, washing with water and freeze-drying, and (e) Optionally sterilizing the freeze-dried product obtained in (d) by γ irradiation or X-ray irradiation.

Step (a) may be performed similarly to the process described in "Example" of EP-B1-1676592 by submitting the peritoneal membranes from young calves or young pigs to washing with water, a basic treatment with 2% sodium hydroxide solution, washing with water, an acid treatment in a 0.5% hydrochloric solution, washing with water until a pH of 3.5 is obtained, shrinking the material with 7% saline solution, washing with water, dehydrating with acetone and degreasing with n-hexane, milling the dry membrane obtained with a cutting mill, sieving through a 0.5-2 mm sieve and suspending the powder obtained in an acidified water solution of pH from 2.5 to 3.5, such as to obtain a slurry of porcine or bovine peritoneum collagen fibres.

Step (a) is conveniently performed by milling the sterile membrane Geistlich Bio-Gide® (obtainable from Geistlich Pharma A.G., Switzerland) with a cutting mill, sieving through a 0.5-2 mm sieve and suspending the powder obtained in an acidified water solution of pH from 2.5 to 3.5, such as to obtain a slurry of porcine peritoneum collagen fibres.

Preferably the powder obtained after milling with a cutting mill is sieved through a 0.5-1 mm sieve.

Step (b) may be performed similarly to the process disclosed in Example 7 of WO 2012/084214 by submitting grinded porcine rinds to a dehydrating treatment with a water soluble organic solvent such as an alcohol or a ketone, a degreasing treatment with an organic solvent such a dichloroethane or methylene chloride, a basic treatment in a strong inorganic base at a pH above 12 for a period of 6 to 24 hours, an acid treatment in a strong inorganic acid at a pH from 0 to 1 for a period of 1 to 12 hours, rinsing with water and suspending the collagen fibres in the presence of a swelling regulator, freeze-drying, cleaning the dried collagen fibres with different organic solvents such as alcohols, ethers, ketones and chlorinated hydrocarbons and grinding in a colloid mill the cleaned dried fibres in an acidified solution of pH from 3 to 4, such as to obtain a slurry of porcine dermis collagen fibres.

The (w/w) % collagen in the slurry of collagen fibres prepared in step (a) and (w/w) % collagen in the slurry of collagen fibres prepared in step (b) play a role in setting the density in dry state of the resilient resorbable chemically crosslinked collagen sponge. Indeed, the latter mainly depends on one side on the (w/w) % collagen of the resulting slurry of collagen fibres obtained in step (c) by mixing 1.5 to 4.5 parts of the slurry of collagen fibres obtained in (a) with 0.5 to 1.5 parts of the slurry of collagen fibres obtained in (b) and on the other side on the conditions of the crosslinking reaction in step (d).

To achieve for the resilient resorbable chemically crosslinked collagen sponge the required density in dry state of 50 to 65 mg/cm$^3$, the slurry of collagen fibres prepared in step (a) contains generally from 2.0 to 4.5, preferably 2.5 to 3.75 (w/w) % collagen and the slurry of collagen fibres prepared in step (b) contains generally from 3.0 to 7.0, preferably 4.0 to 6.0 (w/w) % collagen.

Step (c) comprises mixing 3.5 to 4.5 weight parts of the slurry of collagen fibres obtained in (a) with 0.5 to 1.5 weight parts of the slurry of collagen fibres obtained in (b), such as to obtain a resulting slurry.

This mixing step of appropriate proportions of two different slurries of collagen fibres coming from different porcine or bovine tissues and having been subjected to different treatments including different grinding procedures (using a cutting mill for step (a) and a colloid mill for step (b)) giving collagen fibre particles of different sizes, is a convenient method for attaining the desired porosity distribution or spectrum of the resilient resorbable chemically crosslinked collagen sponge, namely interconnected pores with a median pore diameter between 50 and 90 μm and at least 80%, preferably at least 90% porosity with a pore diameter more than 10 μm as determined by mercury intrusion porosimetry.

The resulting slurry generally contains 3.0 to 6.5 (w/w) %, preferably 3.5 to 6.0 (w/w) % collagen.

Step (d) comprises freeze-drying the resulting slurry obtained in (c), crosslinking the freeze-dried product in a solution containing a crosslinking agent, washing with water and freeze-drying.

Freeze-drying before and after the crosslinking step is generally performed at a temperature below −10° C.

The crosslinking agent is suitably selected from the group consisting of gluteraldehyde, EDC (1-ethyl-3-(3-dimethylaminopropyl)-carbodiimide) and a mixture of EDC and NHS (N-hydoxysuccinimide). Other crosslinking agents known for crosslinking collagen such as formaldehyde, acetaldehyde, 1,4-butane diglycidyl ether (BDDGE), N-sulfosuccinimidyl-6-(4'-azido-2'-nitrophenylamino) hexanoate, hexamethylene diisocyanate (HMDC), cynamide, diphenylphosphorylazide or genipin may also be used.

When the crosslinking agent is gluteraldehyde, the sponge obtained after freeze-drying is suitably chemically crosslinked in a phosphate buffer solution of pH 7.0 to 7.5 containing 0.01 to 0.10%, preferably 0.04 to 0.06% gluteraldehyde. The chemically crosslinked sponge may be successively washed with water, 1-3 M NaCl solution, 0.05-0.15 M $Na_2HPO_4$ solution and water, before being freeze-dried.

When the crosslinking agent is EDC, the sponge obtained after freeze-drying is suitably first submitted to a dehydrothermal treatment at a temperature above 110° C., then chemically crosslinked in a buffer solution containing 0.05-0.15 M MES (2-(N-morpholino)-ethanesulfonic acid) or 0.05-0.15 M acetic acid and 2-20% (w/w) of an alcohol selected from the group consisting of methanol, ethanol, n-propanol, isopropanol and butanol, with 0.03-0.80, preferably 0.2-0.4 g EDC per g collagen, for a period of 1 to 8 hours. The (w/w) ratio of collagen to the reaction medium (the above buffer solution) is generally from 1/10 to 1/100, preferably from 1/20 to 1/50. When the alcohol is ethanol, it is suitably present at 3-7% (w/w) in the buffer solution. The chemically crosslinked collagen sponge may be washed first with 0.05-0.15 M $Na_2HPO_4$ solution, a 0.5-3 M NaCl solution, then with water before being freeze-dried.

When the crosslinking agent is a mixture of EDC and NHS, the sponge obtained after freeze-drying is suitably chemically crosslinked in a buffer solution containing 0.1-0.3 M MES (2-(N-morpholino)-ethanesulfonic acid) or 0.1-0.3 M acetic acid and 10-70% (w/w) alcohol selected from the group consisting of methanol, ethanol, n-propanol, isopropanol and butanol, with 0.01-0.60, preferably 0.05-0.2 g EDC and 0.01-0.6, preferably 0.05-0.2 g NHS, per g collagen, for a period of 1 to 8 hours. The molar ratio of EDC to NHS is generally from 4 to 0.5, preferably from 2 to 1. The (w/w) ratio of collagen to the reaction medium (the above buffer solution) is generally from 1/10 to 1/100, preferably from 1/20 to 1/50. When the alcohol is ethanol, it is suitably present at 40-60% (w/w) in the buffer solution. The chemically crosslinked collagen sponge may be washed first with 0.05-0.15 M $Na_2HPO_4$ solution, then with water before being freeze-dried.

For each mixture of slurries of collagen fibres obtained in (c) the skilled person will be in a position based on the teaching of the present application, using only common general knowledge of the art and routine experimentation, to find the crosslinking agent and the crosslinking conditions such as to obtain a resilient resorbable chemically crosslinked collagen sponge according to the invention having the specified onset temperature and density in dry state.

The following has thus e.g. been found by routine experimentation for collagen slurries containing 3.0 to 6.5 (w/w) % collagen:

When the crosslinking agent is EDC:

- the onset temperature is increased, for a rise of the concentration of EDC in the buffer solution, the ratio of EDC to collagen, the (w/w) ratio of the reaction medium to collagen or the % of alcohol in the buffer solution.
- the density in dry state is decreased (more shrinkage of collagen) for a rise of the % of alcohol in the buffer solution.

When the crosslinking agent is a mixture EDC and NHS:

- the onset temperature is increased, for a rise in the concentration of the crosslinking agent in the buffer solution, the (w/w) ratio of the crosslinking agent (EDC+NHS) to collagen, ratio of EDC to NHS, the (w/w) ratio of the reaction medium to collagen or the % of alcohol in the buffer solution.
- the density in dry state is decreased (more shrinkage of collagen) for a rise of the % of alcohol in the buffer solution.

The freeze-dried resilient resorbable chemically crosslinked collagen sponge obtained at the end of step (d) will generally be submitted to step (e) of sterilization by γ irradiation or X-ray irradiation. That step may not be necessary if the mixture of collagen slurries obtained in step (c) is already aseptic and step (d) is performed under aseptic conditions.

The in vitro cyclic compression test and enzymatic degradation test using collagenase from Clostridium histolyticum, which are described in detail below, are very useful in predicting the in vivo behaviour of the chemically crosslinked sponge after implantation into the oral cavity, notably its capacity of keeping volume and healing without adverse events such as excessive inflammation or dehiscence.

The invention also relates to the above process for preparing the resilient resorbable chemically crosslinked collagen sponge.

The invention also concerns the above resilient resorbable chemically crosslinked collagen sponge for use as an implant for the oral cavity, the use of that resilient resorbable chemically crosslinked collagen sponge for preparing an implant for the oral cavity and a method of augmenting soft tissue volume in the oral region, notably by fostering the ingrowth of gingival cells while keeping volume under mechanical stresses, which comprises implanting into the oral cavity the above resilient resorbable chemically crosslinked collagen sponge.

The following experimental methods, tests and Examples illustrate the invention without restricting its scope.

Test for Determination of the Density of the Resilient Resorbable Chemically Crosslinked Collagen Sponge in Dry State The resilient resorbable chemically crosslinked collagen sponge samples were introduced into tared plastic tubes which are dried in a freeze-drier for at least 2 hours at a temperature of 20° C. and a pressure below 0.5 mbar. The tubes with dried samples were weighed and the net weights of the samples in dry state calculated.

The length, width and height of the resilient resorbable chemically crosslinked collagen sponge samples were measured by using an electrical slide gauge, by applying enough contact pressure such that the samples are loosely fixed (i.e. fixed to resist the force caused by their weight but apt to move when is force is increased about 10-fold). The volumes of the samples in dry state were calculated. The density of the resilient resorbable chemically crosslinked collagen sponge in dry state (weight over volume) was then calculated for each sample.

Cyclic Compression Test

The % of initial thickness and hysteresis in respect to the first loading after 49 cycles of compression to a pressure of 12.1 kPa were measured using a mechanical compression machine, namely Z2.5 material compression machine manufactured by Zwick Roell, using the program Test Expert II.

The measurements were performed submerged in PBS at 37° C. on sterile, resilient resorbable chemically crosslinked collagen sponge samples which had been incubated for 2 hours at 37° C. in a PBS solution of pH 7.4 (prepared by dissolving 80.0 g NaCl, 2.0 g KCl, 17.7 g $Na_2HPO_4$ and 2.4 g $KH_2PO_4$ in 1000 ml water, diluting ten times the solution in water and adjusting the pH with HCl to 7.4).

Samples were subjected to a total of 49 cycles of loading between 0.5 and 12.1 kPa at a strain rate of 33% of initial height per min, analysis starting at a pre-pressure of 0.25 kPa.

The initial height at 0.5 kPa pressure was used to calculate the retention of initial height after 49 cycles of loading and unloading. The "hysteresis in respect to the first loading" is the percentage work which was dissipated during unloading using the work ($W_{1,loading}$ in Nm) between 0.5 and 12.1 kPa of the first loading and the work from the $49^{th}$ unloading cycle ($W_{49,unloading}$ in Nm) according equation XY:

$$\text{"Hysteresis in respect to the first loading" [\%]} = \frac{100*(W_{1,loading} - W_{49,unloading})}{W_{1,loading}} \quad \text{Eq XY}$$

The program Test Expert or Excel calculates the % of retention of initial thickness and the % of retention of initial hysteresis after 49 cycles of compression to a pressure of 12.1 kPa.

The FIGURE shows the typical result of a cyclic compression test.

For samples of the resilient resorbable chemically crosslinked collagen sponge according to the invention that in vivo showed interesting volume retention and healing without excessive inflammation or dehiscence:

- the height or thickness retention in respect of the initial height was at least 70%, preferably at least 80%, more preferably at least 85%, after 49 cycles of compression to 12.1 kPa, and
- the hysteresis retention in respect to the first loading after 49 cycles of compression to 12.1 kPa was less than 55%, preferably less than 45%.

Enzymatic Degradation Test Using Collagenase from Clostridium histolyticum

In the human body collagens are degraded by human tissue matrix-metalloproteinase (MMP), cathepsins and putatively by some serine proteinases. Best studied are the MMPs where collagenases (notably MMP-1, MMP-8, MMP-13 and MMP-18) are the most important enzymes for direct collagen degradation (Lauer-Fields et al. 2002 Matrix metalloproteinases and collagen catabolism in Biopolymers—Peptide Science Section and Song et al. 2006 Matrix metalloproteinase dependent and independent collagen degradation in Frontiers in Bioscience).

Collagenase capability to degrade collagen tissues and membranes depends on the substrate flexibility and collagen type, MMP active sites and MMP exosites.

Collagenases align at the triple helical collagen, unwind it and subsequently cleave it (Song et al. 2006, see above).

With the view of overcoming differences in degradation between the different collagen types, collagenase degradation of collagen is often assessed using collagenase from Clostridium histolyticum which has a high catalytic speed (Kadler et al. 2007 Collagen at a glance in J Cell Sci). Generally, a natural collagen product degrades faster than a chemically cross-linked collagen product.

In this test the collagen products (samples of resilient resorbable chemically crosslinked collagen sponge according to the invention were incubated at 37° C. with 50 units/ml from Clostridium histolyticum (one unit being defined as liberating peptides from collagen from bovine Achilles tendon equivalent in ninhydrin color to 1.0 micromole of leucine in 5 hours at pH 7.4 at 37° C. in the presence of calcium ions) in a calcium containing Tris-buffer and the degradation of the collagen matrix was measured visually and with the "DC Protein Assay" from Bio-Rad Laboratories (Hercules, USA, Order Nr. 500-0116) using Collagen Type I as reference material. The collagen concentration was determined using a microwellplate spectrometer (Infinite M200, available from Tecan).

For samples of the resilient resorbable chemically crosslinked collagen sponge according to the invention that in vivo showed healing without excessive inflammation or dehiscence, the collagen was completely degraded (no collagen fibre detectable by visual inspection) within 3 to 5 hours.

EXAMPLE 1

Preparation of a Slurry of Collagen Fibres Derived from Porcine Peritoneum

The peritoneal membranes from young pigs were completely freed from flesh and grease by mechanical means, washed under running water and treated with 2% NaOH solution for 12 hours. The membranes were then washed under running water and acidified with 0.5% HCl. After the material had been acidified through its entire thickness (about 15 min) the material was washed until a pH of 3.5 was obtained. The material was then shrunk with 7% saline solution, neutralised with 1% $NaHCO_3$ solution and washed under running water. The material was then dehydrated with acetone and degreased with n-hexane.

The material was dried using ethanol ether and milled with a cutting mill (e.g. Pulverisette 25 from Fritsch: see fetsch.de./produkte/mahlen/schneidmuehlen/pulverisette-25 or SM300 from Retsch: retsch.de/de/produkte/zerkleinern/schneidmuehlen) which includes a trapezoidal sieve of 0.5 to 1.0 mm.

A 4% (w/w) slurry of collagen fibres and a 6% (w/w) slurry of collagen fibres were prepared by suspending adequate amounts of the dried powder in water and adjusting the pH to 2.6 with 10 mM hydrochloric acid.

EXAMPLE 2

Preparation of a Slurry of Collagen Fibres Derived from a Sterile Geistlich Bio-Gide® Membrane A Geistlich Bio-Gide® membrane (available from Geistlich Pharma AG, CH-6110, Switzerland) was dried and milled with a cutting mill which includes a trapezoidal sieve of 0.5 to 1.0 mm. A 4% (w/w) collagen slurry of collagen fibres and a 6% (w/w) collagen slurry of collagen fibres were prepared by suspending adequate amounts of the dried powder in water and adjusting the pH to 2.6 with 10 mM hydrochloric acid.

EXAMPLE 3

Preparation of a Slurry of Collagen Fibres Derived from Pig Dermis

Porcine hides were ground in a meat grinder to pieces of 1 to 20 mm. The water was removed using a water soluble solvent such as an alcohol or a ketone. The collagen fibres were defatted using a chlorinated hydrocarbon such as dichloroethane or methylene chloride or a non-chlorinated hydrocarbon such as hexane or toluene. After removing the solvent the collagen was treated with a strong inorganic base at a pH above 12 for a period of 6 to 24 hours and treated with a strong inorganic acid at a pH of 0 to 1 for a period of 1 to 12 hours. The excess acid was removed by rinsing with water and the suspension was homogenized by colloid milling to a 0.5 to 2% homogenous suspension of collagen fibres in the presence of a swelling regulator such as an inorganic salt. The suspension was dried by freeze-drying and the dry collagen fibres were successively cleaned with different organic solvents such as alcohols, ethers, ketones and chlorinated hydrocarbons, the solvents being then evaporated under vacuum to a solvent residue of less than 1% (w/w).

A 2.5% (w/w) collagen slurry of collagen fibres and a 3.75% (w/w) collagen slurry of collagen fibres were prepared by finely grinding by colloid milling adequate amounts of the cleaned dry fibres obtained above with water at a pH of 3.4.

EXAMPLE 4

Preparation of a Resilient Resorbable Collagen Sponge Chemically Crosslinked with EDC 4 parts of the 4% (w/w) collagen slurry of collagen fibres obtained in Example 1 or Example 2 were mixed with 1 part of the 2.5% (w/w) collagen slurry of collagen fibres obtained in Example 3 and poured into molds of 8×25×25 mm. The resulting 3.7% slurry of collagen fibres was dried by freeze-drying at −45° C.

The dried collagen sponges were then dehydrothermally treated at 120° C. for 24 hours under reduced pressure (less than 200 mbar).

The collagen sponges were then chemically crosslinked in a buffer solution containing 0.1 M MES (2-(N-morpholino)-ethanesulfonic acid) and 5% ethanol at a pH of 5.5 with 0.3 g EDC (1-ethyl-3-(3-dimethylaminopropyl)carbodiimide) per g collagen, under agitation at room temperature for a period of 120 min.

The chemically crosslinked collagen sponges were washed first with 0.10 M Na2HPO4 solution, 1M NaCl solution, 2M NaCl solution, then with water and freeze-dried at −45° C.

The dried chemically crosslinked collagen sponges were gamma-sterilized at 30 kGy. The measured onset temperature and density in dry state of the sterilized chemically crosslinked collagen sponges were 47° C. and 64 mg/cm$^3$, respectively.

After 49 cycles of compression to a pressure of 12.1 kPa in PBS at 37° C., the sterilized chemically crosslinked collagen sponges showed a retention of 87% of its initial thickness and 41% of the initial hysteresis.

Mercury intrusion porosimetry showed for the sterilized chemically crosslinked collagen sponges a median pore diameter of 88 μm and 95% porosity with a pore diameter more than 10 μm.

The enzymatic degradation test using collagenase from Clostridium histolyticum showed a complete degradation of collagen within 3.25 hours.

EXAMPLE 5

Preparation of a Resilient Resorbable Collagen Sponge Chemically Crosslinked with a Mixture of EDC and NHS Four parts of the 6% (w/w) slurry of collagen fibres obtained in Example 1 or Example 2 were mixed with one part of the 3.75% (w/w) slurry of collagen fibres obtained in Example 3 and poured into molds of a height of 6 mm. The resulting 5.55% (w/w) collagen slurry of collagen fibres was dried by freeze drying at −10° C. These sponges were chemically crosslinked in a solution containing 0.2 M MES (2-(N-morpholino)-ethanesulfonic acid) and 50% w/w ethanol at a pH of 5.5 with 0.1 g EDC (1-ethyl-3-(3-dimethylaminopropyl)-carbodiimide) per gram collagen and 0.1 g NHS (N-hydoxysuccinimide) per gram collagen, under agitation at room temperature for a period of 120 min. The chemically crosslinked sponges were washed first with 0.1 M $Na_2HPO_4$ solution, 1M NaCl solution, 2M NaCl solution, then with water and freeze dried at −10° C.

The dried chemically crosslinked collagen sponges were sterilized by γ-irradiation at 26 kGy.

The measured onset temperature and density in dry state of the sterilized chemically crosslinked collagen sponges were 52° C. and 59 mg/cm$^3$, respectively. After 49 cycles of compression to a pressure of 12.1 kPa in PBS at 37° C., the sterilized chemically crosslinked collagen sponges showed a retention of 90% of its initial thickness and 38% of the hysteresis in respect of the first loading. Mercury intrusion porosimetry showed for the sterilized chemically crosslinked collagen sponges a median pore diameter of 69.1 μm and 93.1% porosity with a pore diameter more than 10 μm.

The enzymatic degradation test using collagenase from Clostridium histolyticum showed a complete degradation of collagen within 3.5 hours.

EXAMPLE 6

Preparation of a Resilient Resorbable Collagen Sponge Chemically Crosslinked with a Mixture of EDC and NHS (without a Sterilization Step)

Four parts of the 6% (w/w) slurry of collagen fibres obtained in Example 2 were mixed with one part of the 3.75% (w/w) slurry of collagen fibres obtained in Example 3 and poured into molds of a height of 6 mm. The resulting 5.55% (w/w) collagen slurry of collagen fibres was dried by freeze drying at −10° C.

These sponges were chemically crosslinked in a solution containing 0.2 M MES (2-(N-morpholino)-ethanesulfonic acid) and 50% w/w ethanol at a pH of 5.5 with 0.01 g EDC (1-ethyl-3-(3-dimethylaminopropyl)-carbodiimide) per gram collagen and 0.01 g NHS (N-hydoxysuccinimide) per gram collagen, under agitation at room temperature for a period of 120 min. The chemically crosslinked sponges were washed first with 0.1 M $Na_2HPO_4$ solution, 1M NaCl solution, 2M NaCl solution, then with water and freeze dried at −10° C.

The measured onset temperature and density in dry state of the chemically crosslinked collagen sponges were 57° C. and 57 mg/cm$^3$ respectively.

After 49 cycles of compression to a pressure of 12.1 kPa in PBS at 37° C., the chemically crosslinked collagen sponges showed a retention of 80% of its initial thickness.

Mercury intrusion porosimetry showed for the chemically crosslinked collagen sponges a median pore diameter of 71.0 μm and 94.0% porosity with a pore diameter more than 10 μm.

EXAMPLE 7

Preparation of a Resilient Resorbable Collagen Sponge Chemically Crosslinked with Glutaraldehyde Four parts of the slurry of collagen fibres obtained in Example 1 were mixed with one part of the slurry of collagen fibres obtained in Example 3 and poured into molds of a height of 6 mm. The collagen slurry was dried by freeze drying at minus 45° C. These sponges were chemically crosslinked in a sodium phosphate buffer (pH 7.0-7.5) containing 0.05% (w/w) glutaraldehyde at 10° C. for 60 min. The chemically crosslinked collagen sponges were successively washed with water, 2 M NaCl solution and 0.1 M $Na_2HPO_4$ solution. After the final rinse with water the sponges were freeze dried at −45° C.

The chemically crosslinked collagen sponges were sterilized by γ-irradiation at 25 kGy.

The measured onset temperature and density in dry state of the sterilized chemically crosslinked collagen sponges were respectively 51° C. and 52 mg/cm$^3$.

After 49 cycles of compression to a pressure of 12.1 kPa at 37° C., the sterilized chemically crosslinked collagen sponges in PBS showed a retention of 74% of their initial thickness and 48% hysteresis in respect of the first loading.

Mercury intrusion porosimetry showed for the sterilized chemically crosslinked collagen sponges a median pore diameter of 63.7 μm and 92.7% porosity with a pore diameter more than 10 μm.

The enzymatic degradation test using collagenase from Clostridium histolyticum showed a complete degradation of collagen within 4.5 hours.

The invention claimed is:

1. A resilient resorbable chemically crosslinked collagen sponge for promoting soft tissue volume augmentation in an oral cavity, comprising 60-96% (w/w) collagen and 4-40% (w/w) elastin, which shows by mercury intrusion porosimetry interconnected pores with a median pore diameter between 50 and 90 μm and at least 80% porosity with a pore diameter more than 10 μm, an onset temperature of 45 to 57° C. and a density in dry state from 50 to 65 mg/cm$^3$.

2. The resilient resorbable chemically crosslinked collagen sponge of claim 1 which shows an onset temperature from 46 to 53° C.

3. The resilient resorbable chemically crosslinked collagen sponge of claim 1, which shows a density in dry state from 50 to 60 mg/cm$^3$.

4. The resilient resorbable chemically crosslinked collagen sponge of claim 1, which comprises 70-90% (w/w) collagen and 10-30% (w/w) elastin.

5. The resilient resorbable chemically crosslinked collagen sponge of claim 1, which shows at least 90% porosity with a pore diameter more than 10 μm.

6. The resilient resorbable chemically crosslinked collagen sponge of claim 1, which was obtained using a crosslinking agent selected from the group consisting of gluteraldehyde, EDC (1-ethyl-3-(3-dimethylaminopropyl)-carbodiimide) and a mixture of EDC and NHS (N-hydoxysuccinimide).

7. The resilient resorbable chemically crosslinked collagen sponge of claim 1, which was derived from tissues of natural origin by a process comprising freeze drying and chemical crosslinking, optionally followed by γ-sterilization or X-ray sterilization.

8. The resilient resorbable chemically crosslinked collagen sponge of claim 7, wherein the tissues of natural origin include porcine or bovine peritoneum or pericardium membranes, porcine or bovine placenta membrane, or porcine or bovine SIS or dermis.

9. The resilient resorbable chemically crosslinked collagen sponge of claim 1, which wetted by a PBS solution retains at least 70% of initial thickness after 49 cycles of compression to a pressure of 12.1 kPa.

10. The resilient resorbable chemically crosslinked collagen sponge of claim 1, which wetted by a PBS solution retains less than 55% hysteresis with respect to the first loading after 49 cycles of compression to a pressure of 12.1 kPa.

11. The resilient resorbable chemically crosslinked collagen sponge of claim 1, which shows after implantation in the oral cavity the same volume retention as SCTG (Subepithelial Connective Tissue Graft).

12. A process for making the resilient resorbable chemically crosslinked collagen sponge of claim 1, which comprises the following steps:

(a) submitting a porcine or bovine peritoneum or pericardium membrane to a basic treatment in a sodium hydroxide solution at a pH above 12, an acid treatment in a hydrochloric solution of pH of 1 to 3, a dehydrating treatment with a water soluble organic solvent and a degreasing treatment with an organic solvent, milling the dry membrane obtained with a cutting mill, sieving through a 0.5-2 mm sieve and suspending the powder obtained in an acidified water solution of pH from 2.5 to 3.5, [such as] to obtain a first slurry of collagen fibres, (b) *separately from step (a)* submitting grinded bovine or porcine dermis to a dehydrating treatment with a water soluble organic solvent, a degreasing treatment with an organic solvent, a basic treatment in a strong inorganic base at a pH above 12, an acid treatment in a strong inorganic acid at a pH from 0 to 1, rinsing with water and suspending the collagen fibres, freeze-drying, cleaning the dried collagen fibres with an organic solvent and grinding the cleaned dried fibres in an acidified solution of pH from 3 to 4, [such as] to obtain a second slurry of collagen fibres, (c) mixing 3.5 to 4.5 parts of the collagen fibres slurry obtained in (a) with 0.5 to 1.5 parts of the collagen fibres slurry obtained in (b), [such as] to obtain a resulting slurry, (d) freeze-drying the resulting slurry obtained in (c) to obtain a first freeze-dried product, and crosslinking the first freeze-dried product in a solution containing a crosslinking agent, washing with water and freeze-drying to obtain a second freeze-dried product, and (e) optionally sterilizing the second freeze-dried product obtained in (d) by γ irradiation or X-ray irradiation.

13. The process according to claim 12, wherein the crosslinking agent is selected from the group consisting of gluteraldehyde, EDC (1-ethyl-3-(3-dimethylaminopropyl)-carbodiimide) and a mixture of EDC and NHS (N-hydoxysuccinimide).

14. The process according to claim 12, wherein the slurry of collagen fibres prepared in step (a) contains 2.5 to 3.75 (w/w) % collagen and the slurry of collagen fibres prepared in step (b) contains from 4.0 to 6.0 (w/w) % collagen.

15. A method of promoting soft tissue volume augmentation in an oral cavity of a subject in need thereof, comprising implanting the resilient resorbable chemically crosslinked collagen sponge of claim 1 into said subject's oral cavity to promote tissue volume augmentation.

*16. An implant comprising a sterile resilient resorbable chemically crosslinked collagen sponge that is resistant to cyclic compression, comprising 60-96% (w/w) collagen and 4-40% (w/w) elastin, which shows by mercury intrusion porosimetry interconnected pores with a median pore diameter between 50 and 90 μm and at least 80% porosity with a pore diameter more than 10 μm, an onset temperature of 45 to 57° C. and a density in dry state from 50 to 65 mg/cm$^3$.*

*17. The implant of claim 16, wherein the sterile resilient resorbable chemically crosslinked collagen sponge has an onset temperature from 46 to 53° C.*

*18. The implant of claim 16, wherein the sterile resilient resorbable chemically crosslinked collagen sponge has a density in dry state from 50 to 60 mg/cm$^3$.*

*19. The implant of claim 16, wherein the sterile resilient resorbable chemically crosslinked collagen sponge comprises 70-90% (w/w) collagen and 10-30% (w/w) elastin.*

*20. The implant of claim 16, wherein the sterile resilient resorbable chemically crosslinked collagen sponge has at least 90% porosity with a pore diameter more than 10 μm.*

*21. The implant of claim 16, wherein the sterile resilient resorbable chemically crosslinked collagen was obtained using a crosslinking agent selected from the group consisting of gluteraldehyde, EDC (1-ethyl-3-(3-dimethylaminopropyl)-carbodiimide) and a mixture of EDC and NHS (N-hydoxysuccinimide).*

*22. The implant of claim 16, wherein the sterile resilient resorbable chemically crosslinked collagen sponge was derived from tissues of natural origin by a process comprising freeze drying and chemical crosslinking, optionally followed by γ-sterilization or X-ray sterilization.*

*23. The implant of claim 22, wherein the tissues of natural origin include porcine or bovine peritoneum or pericardium membranes, porcine or bovine placenta membrane, or porcine or bovine SIS or dermis.*

*24. The implant of claim 16, when wetted by a PBS solution retains at least 70% of initial thickness after 49 cycles of compression to a pressure of 12.1 kPa.*

*25. The implant of claim 16, when wetted by a PBS solution retains less than 55% hysteresis with respect to the first loading after 49 cycles of compression to a pressure of 12.1 kPa.*

*26. The implant of claim 16, having properties such that the collagen completely degrades within 3 to 5 hours in an enzymatic degradation test using collagenase from Clostridium histolyticum.*

*27. The implant of claim 16, wherein the sterile resilient resorbable chemically crosslinked collagen sponge comprises 70-90% (w/w) collagen and 10-30% (w/w) elastin, which shows by mercury intrusion porosimetry interconnected pores with a median pore diameter between 50 and 90 μm and at least 90% porosity with a pore diameter more than 10 μm, an onset temperature of 46 to 53° C. and a density in dry state from 50 to 60 mg/cm$^3$.*

* * * * *